United States Patent
Oliva et al.

(10) Patent No.: US 6,335,332 B1
(45) Date of Patent: Jan. 1, 2002

(54) BARBITURIC ACID DERIVATIVES WITH ANTIMETASTATIC AND ANTITUMOR ACTIVITY

(75) Inventors: Ambrogio Oliva, Saronno; Gianpiero De Cillis, Trezzo Sull'Adda, both of (IT); Frank Grams, Neuenburg-Zinken (DE); Valeria Livi, Sesto S. Giovanni (IT); Gerd Zimmermann, Linkenheim (DE); Ernesto Menta, Cernusco sul Naviglio (IT); Hans-Willi Krell, Penzberg (DE)

(73) Assignee: Roche Diagnostics GmbH, Mannheim (DE)

( * ) Notice: Subject to any disclaimer, the term of this patent is extended or adjusted under 35 U.S.C. 154(b) by 0 days.

(21) Appl. No.: 09/445,461
(22) PCT Filed: Jun. 18, 1998
(86) PCT No.: PCT/EP98/03677
§ 371 Date: Apr. 3, 2000
§ 102(e) Date: Apr. 3, 2000
(87) PCT Pub. No.: WO98/58925
PCT Pub. Date: Dec. 30, 1998

(30) Foreign Application Priority Data

Jun. 21, 1997 (EP) .......................... 97110200

(51) Int. Cl.$^7$ .................. A61K 31/515; A61P 35/04; C07D 239/62; C07D 403/06
(52) U.S. Cl. .............. 514/227.8; 514/270; 544/60; 544/299; 544/300; 544/301
(58) Field of Search ................. 544/299, 300, 544/301, 60; 514/270, 227.8

(56) References Cited

U.S. PATENT DOCUMENTS 6,110,924 A 8/2000 Bosies et al. ............... 544/123

FOREIGN PATENT DOCUMENTS

EP 0 457 213 11/1991
WO 91 08191 6/1991

OTHER PUBLICATIONS

Paolo Tecilla: "Synthetic Hydrogen Bonding Receptors", Tetrahedron, vol. 51, No. 2, 1995, pp. 435–448.
Chemical Abstracts, vol. 116, No. 28, 1992, Abstract No. 106216d, A. Talab et al., Chromic Oxydation and Synthesis of Metabolits of Barbituratures, pp. 769, vol. 46, No. 5, 1991, pp. 293–300.
Chemical Abstracts., vol. 83, No. 1, 1975, Abstract No. 201710u, N. Haskins et al., "Qualitat. and Quantitat. Investigation of Barbituarates Metabolites", pp. 3, vol. 6, 1974, pp. 181–186.
Chemical Abstracts., vol. 97, No. 1, 1982, Abstract No. 16559c., M. Al Sharifi et al., "The Effect of Antimebic Drug Therapy on the Metabolism of Butobarbitone", p. 13, J. Pharm. Pharmacol, vol. 34, No. 2, 1982, pp. 126–127.
M. Adamczyk et al. "Synthesis of Conjugates ofr a Barbiturate Screening Assay", Bioconjugate Chemistry., vol., 8, No. 3, 1997, pp. 281–288.

Primary Examiner—Mukund J. Shah
Assistant Examiner—Venkataraman Balasubramanian
(74) Attorney, Agent, or Firm—Arent Fox Kintner Plotkin Kahn

(57) ABSTRACT

The invention is directed to barbituric acid derivatives having inhibitory activity for matrix maetalloproteases comprised of formula (I):

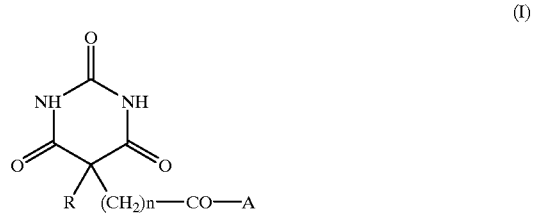

(I)

pharmaceutical compositions thereof, processes for preparing the derivatives, and methods for treating diseases associated with elevated or uncontrolled levels of matrix metalloprotease activity, e.g., cancer, specifically tumor progression and tumor metastasis, inflammation, or as a method of contraception.

8 Claims, No Drawings

BARBITURIC ACID DERIVATIVES WITH ANTIMETASTATIC AND ANTITUMOR ACTIVITY

The present invention relates to new derivatives of the barbituric acid 5,5-bis-substituted. These compounds showed a marked antimetastatic and antitumor activity.

BACKGROUND OF THE INVENTION

In the past the therapy of the tumors has been achieved by surgical intervention, radiation treatment and chemotherapy. The drawbacks of this latter are mainly due to the toxicity of the cytotoxic drugs, which is usually not restricted to the cancer cells, and to the acquired resistance of the cancer cells to some of the most widely used drugs, which varifies the final result of the therapy.

On the other hand, the elimination of the primary tumor by surgery is not always possible and in any case does not prevent the most metastasizing tumors, such as for example breast cancer or melanoma, to invade other target organs, which develop further secondary tumors after months or years from the surgical treatment. These secondary tumors are usually the main cause of death in the patient.

In the years it has become apparent that the therapy of the metastasizing tumors is unlikely to bring the complete cure of the patient: therefore, the treatment with cytotoxic drugs is now seen as a palliative and life-prolonging method rather than a curative method. A croncial treatment with a drug having low toxicity would be preferable while targeted to the control of the progression of the disease. An example of such therapy is the treatment of invasive breast cancer with tamoxifen.

The efforts of many researchers have been focused recently to the development of drugs able to inhibit the invasive process of the tumor which brings to metastases formation. Among the targets that have been evaluated up to now to give rise to a possible antimetastatic activity, the inhibition of the matrix metalloproteinases seems to be one of the most promising.

The matrix metalloproteinases (or metalloproteases), which are upregulated in the cancer cells, degrade the extracellular matrix and bring to the propagation of the tumor cells into the blood stream to reach the target organs where the metastasis develop. Moreover, they are associated with tumor growth and angiogenesis. Nevertheless, since different types of such proteases exist in the organism and are implicated in the regulation of vital functions, selected inhibition of certain combination of MMPs is desired, in order to avoid toxic side effects, especially in a chronical treatment.

A number of compounds are known in the literature [see review article: Beckett et al., DDT 1, 16 (1996)] or are described in the patent literature [WO-A-92/09563 by Glycomed, EP-A-497 192 by Hoffmann-LaRoche, WO-A-90/05719 by British Biotechnology, EP-A-489 577 by Celltech, EP-A-320 118 by Beecham, U.S. Pat. No. 4,595,700 by Searle]. In particular, batimastat and marimastat have been developed by British Biotechnology and the latter is now under investigation in clinical trials. However, such compounds are broad inhibitors of matrix metalloproteinases, therefore therapy with these molecules might be associated to undesirable toxicity.

It is therefore evident that there is still a high need of new compounds, which must have a low toxicity and a marketed activity in inhibiting both the tumor growth and the metastasis process, as candidates for a chronical antitumor therapy.

We have now found a new class of compounds that possesses a marked inhibitory activity against the matrix metalloproteinases and showed antimetastatic and antitumor activity.

DESCRIPTION OF THE INVENTION

The present invention relates to compounds of the general formula (I):

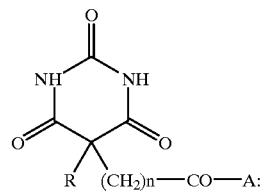

R (CH$_2$)n—CO—A:

wherein:
R is a W-V group, in which W is a bond or a linear or branched (C$_1$–C$_8$)alkyl or a (C$_2$–C$_8$)alkenyl; V is a monocycle to bicycle, saturated or unsaturated, which can optionally contain from 1 to 3 heteroatoms selected from nitrogen, oxygen or sulfur and which can be optionally substituted by a (C$_1$–C$_4$)alkoxy, phenoxy or phenyl group: or W-V is a (C$_1$–C$_{20}$)alkyl group which can be optionally interrupted or terminated by one or more heteroatoms selected from oxygen or sulfur or by a —N(R$^5$)— group, in which R$^5$ is selected from hydrogen, (C$_1$–C$_4$)alkyl or (C$_1$–C$_4$)acyl.

n is an integer from 1 to 3;

A is selected from the following groups: R$^1$, —N(R$^2$)—(CH$_2$)$_m$—N(R$^9$)—T—R$^{10}$, —N(R$^2$)—CHR$^6$—CO—R$^7$, —N(R$^2$)—T—NR$^3$R$^4$, in which
T is a —CO— or —SO$_2$— group;
m is an integer from 2 to 6;
R$^1$ is selected from —OH, (C$_1$–C$_4$)alkoxy,—NH$_2$, mono- or di-(C$_1$–C$_4$)alkylamino, benzylamino, phenoxy or benzyloxy groups, these two latter being optionally substituted with one or more groups selected from (C$_1$–C$_4$)alkyl, (C$_1$–C$_4$)alkoxy, halogen, —OH, —NH$_2$, mono- or di-(C$_1$–C$_4$) alkylamino, nitro, (C$_1$–C$_4$)alkylsulphonyl, (C$_1$–C$_4$) alkylsulphonamido; or is a group of formula —N(R$^9$)—CO—R$^{10}$ in which R$^9$ and R$^{10}$, taken together with the N—CO group to which they are linked, form a 5- to 7-membered lactam, which can optionally be benzocondensed and/or substituted with a group selected from (C$_1$–C$_4$)alkyl, (C$_1$–C$_4$) alkoxy, halogen, —OH, —NH$_2$, mono- or di-(C$_1$–C$_4$)alkylamino, nitro, (C$_1$–C$_4$)alkylsulphonyl, (C$_1$–C$_4$)alkylsulphonamido,
R$^2$ is selected from hydrogen, (C$_1$–C$_4$)alkyl, (C$_3$–C$_7$) cycloalkyl, (C$_3$–C$_7$)cycloalkyl-(C$_1$–C$_4$)alkyl, phenyl or benzyl groups, these two latters being optionally substituted with one or more groups selected from (C$_1$–C$_4$)alkyl, (C$_1$–C$_4$)alkoxy, halogen, —OH,—NH$_2$, mono- or di-(C$_1$–C$_4$)alkylamino, nitro, (C$_1$–C$_4$)alkylsulphonyl, (C$_1$–C$_4$)alkylsulphonamido; or R$^2$ is a Het-(C$_1$–C$_2$)alkyl group, in which Het is a 5- or 6-membered heterocycle having from 1 to 3 heteroatoms selected from nitrogen, oxygen or sulfur, which can be optionally benzocondensed;
R$^3$ is selected from hydrogen, (C$_1$–C$_4$)alkyl, (C$_3$–C$_7$) cycloalkyl, phenyl, benzyl or phenetyl, which can be optionally substituted by a group selected from (C$_1$–C$_4$)alkoxy, —SO$_2$NH$_2$.

R⁴ is a —(CH₂)ₚ—B group, wherein p is 0, 1 or 2 and B is selected from (C₁-C₄)alkyl; benzyldryl; monocycle or bicycle, saturated or unsaturated, which can optionally be benzocondensed and/or substituted with a group selected from (C₁-C₄)alkyl, (C₁-C₄) alkoxy, halogen, —OH,—NH₂, mono- or di-(C₁-C₄) alkylamino, nitro, (C₁-C₄)alkylsulphonyl, (C₁-C₄) alkylsulphonamido; 5- or 6-membered heterocycle having from 1 to 3 heteroatoms selected from nitrogen, oxygen or sulfur, which can be optionally benzocondensed and/or substituted with a group selected from (C₁-C₄)alkyl, (C₁-C₄)alkoxy, halogen, —OH, —NH₂mono- or di-(C₁-C₄) alkylamino, nitro, (C₁-C₄)alkylsulphonyl, (C₁-C₄) alkylsulphonamido; or R³ and R⁴, taken together with the nitrogen atom to which they are linked, form a 5- or 6-membered heterocycle having from 1 to 3 heteroatoms selected from nitrogen, oxygen or sulfur, which can be optionally benzocondensed and/or substituted with a group selected from (C₁-C₄) alkyl, (C₁-C₄)alkoxy, halogen, —OH, —NH₂, mono- or di-(C₁-C₄)alkylamino, nitro, (C₁-C₄) alkylsulphonyl, (C₁-C₄)alkylsulphonamido;

R⁶ is a —(CH₂)_q-D group in which q is 0, 1 or 2 and D is selected from hydrogen; (C₁-C₄)alkyl; a monocycle or bicycle, saturated or unsaturated, which can optionally be benzocondensed and/or substituted with a group selected from (C₁-C₄)alkyl, (C₁-C₄) alkoxy, halogen, —OH, —NH₂, mono- or di-(C₁-C₄)alkylamino, nitro, (C₁-C₄)alkylsulphonyl, (C₁-C₄)alkylsulphonamido; 5- or 6-membered heterocycle having from 1 to 3 heteroatoms selected from nitrogen, oxygen or sulfur, which can be optionally benzocondensed and/or substituted with a group selected from (C₁-C₄)alkyl, (C₁-C₄)alkoxy, halogen, —OH, —NH₂, mono- or di-(C₁-C₄) alkylamino, nitro, (C₁-C₄)alkylsulphonyl, (C₁-C₄) alkylsulphonamido;

R⁷ is selected from —OH, (C₁-C₈)alkoxy, —NHR³, —NH—CH(R⁶)—COR⁸, in which R⁸ on its turn is selected from —OH, (C₁-C₈)alkoxy or —NHR³ and R³ is as above defined;

R⁹ and R¹⁰ have the same meanings as R³ and R⁴, respectively, but when they are taken together with the N—CO group to which they are linked, they form a 5- to 7-membered lactam, which can optionally be benzocondensed and/or substituted with a group selected from (C₁-C₄)alkyl, (C₁-C₄)alkoxy, halogen, —OH, —NH₂, mono- or di-(C₁-C₄) alkylamino, nitro, (C₁-C₄)alkylsulphonyl, (C₁-C₄) alkylsulphonamido.

The present invention also encompasses enantiomers, racemates, diastereoisomers, tautomers of the compounds of formula (I) or mixtures thereof, as well as their salts with pharmaceutically acceptable acids or bases.

These compounds are endowed with a marked activity as inhibitors of the matrix metalloproteinases.

In the meanings of the present invention, "halogen" means an atom selected from chlorine, bromine, iodine or fluorine.

With the terms "monocycle" or "bicycle" are intended cycloalkanes or aryl groups, such as for example cylopropyl, cyclopentyl, cyclohexyl, decalinyl, phenyl, or naphtalenyl groups. Preferred examples of alkyl groups are methyl, ethyl, n-propyl, isopropyl, n-butyl, tert-butyl, n-hexyl, n-heptyl or n-octyl Preferred examples of 5- or 6-membered heterocycles, optionally benzocondensed, are pyrrolidine, piperidine, morpholine, tiomorpholine, piperazine, pyrane, oxadiazole, tiophene, furane, pyrazole, imidazole, thiazole, pyridine, pyrazine, pyrimidine, indole, indazole, quinoline, isoquinoline, benzopyrimidine, benzopyrazine, benzofurane, benzothiophene, benzothiazole, benzopyrane.

Preferred examples of lactams, optionally benzocondensed, are pyrrolidinone, caprolactam, phtalimide, benzisothiazol-3(2 H)one-1,1-dioxide, 2-imidazolinone, benzopyrimidin-2,4-dione, benzopyrimidin-4-one, 8-azaspiro[4,5]decane-7,9-dione, piperidine-2,3-dione. Preferred compounds of formula (I) are those in which n is 1, A is a R¹ or a —N(R²)—(CH₂)_m—N(R⁹)—COR¹⁰ group and R is selected from a (C₆-C₂₀)alkyl, biphenyl, phenoxyphenyl or (C₁-C₄)alkoxyphenyl group. Particularly preferred are those in which m is 2 and R² is a (C₁-C₄)alkyl, phenyl or benzyl group.

Another object of the present invention is to provide a method for the preparation of the compounds of formula (I).

A further object of the present invention is the use of the compounds of formula (I) in the treatment of those diseases which are susceptible of treatment with inhibitors of the matrix metalloproteinases, as well as pharmaceutical compositions containing effective dosages of one or more compounds of formula (I) in admixture with suitable excipients and/or diluents.

PREPARATION OF THE COMPOUNDS OF THE INVENTION

The compounds of formula (I) can be prepared according to the following multi-step process:

(a) reacting a compound of formula (II):

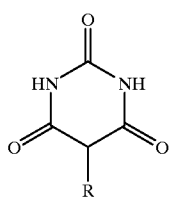

(II)

in which R has the above meanings, with a reactant of formula (III):

X—(CH₂)ₙ—COR¹     (III)

in which n and R¹ have the above meanings, but R¹ is preferably an ester group, and X is a leaving group such as for example a chlorine, bromine or iodine atom or a p-toluensulphonyloxy or a methanesulphonyloxy group. The reaction is usually performed in a solvent and in the presence of an inorganic or organic base, at temperatures ranging from 0° C. to 100° C., preferably between room temperature and 50° C. Preferred reaction conditions are the use of an aprotic dipolar solvent and of an alkaline or alkaline-earth metal carbonate.

(b) removing the R¹ ester group, for example by alkaline hydrolysis in the case of an alkyl ester or by hydrogenolysis in the case of a benzyl ester.

(c) functionalizing the carboxy group in the compound obtained from step (b) with ammonia, mono- or di-(C₁-C₄) alkylamine or an intermediate of formula (IV) HR(R²)—(CH₂)_m—N(R⁹)—T—R¹⁰. (V) HN(R²)—CHR⁶—CO-R⁷. (VI) HN(R²)—T—NR³R⁴ or (VII) HN(R⁹)—COR¹⁰, in which R², R³, R⁴, R⁶, R⁷, R⁹, R¹⁰ and m have the above meanings. This reaction is performed by activating the carboxy group in the usual ways, such as for example as acyl chloride (which can be obtained from the carboxy derivative by means of thionyl chloride). N-hydroxysuccinimido ester (obtainable by reaction of the carboxy group with N-hydroxyssuccinimide in the presence of morpholinoethyl isonitrile), imidazolide derivative (obtainable by reaction of the carboxy group with carbonyl diimidazole) and the like or by condensing the carboxy derivative with the intermediates of formula (IV), (V) or (VI) in the presence of a condensing agent such as dicyclohexyl carbodiimide and the like. Specific examples of such reaction with urea derivatives of formula (IV) are reported in Z. Chem., 25, 389–9 (1985). J. Med. Chem. 23, 857–861 (1980) and J. Indian Chem. Soc., 70(6), 597–9 (1993), which are herein incorporated by reference.

(d) optionally separating the enantiomers or the diastereoisomers of the compounds of formula (I) by means of the usual methods such as column chromatography or crystallization or optical resolution of enantiomers by treatment with optically active acids or basis.

(e) optionally salifying the compounds of formula (I) obtained from steps (a), (b) or (c) with pharmaceutically acceptable acids or basis.

An alternative method for obtaining the compounds of formula (I) in which A is a —N($R^2$)—CO—N$R^3R^4$ and $R^3$ is hydrogen is to react a carboxy derivative of formula (I) (A=OH) or the acyl chloride or bromide thereof with a diimide of formula (IX) $R^2$N=C=N$R^4$ in a solvent and at temperatures ranging from 0° C. to 50° C., more preferably at room temperature. Example of such a reaction can be found in Synthesis, 11, 954 (1991). J. Het. Chem., 22(4), 1009–10 (1985). Arch Pharm., 318(12), 1052–70 (1985), Helv. Chim. Acta. 70(1), 262–70 (1987), Eur. J. Med. Chem., 24, 421–6 (1989) and J. Org. Chem., 54, 2428–32 (1989), which are herein incorporated by reference.

The compounds of formula (II) are known compounds or can be prepared according to methodologies well known to the expert in the art. For example, the synthesis of 5-phenyl barbituric acid is reported in Acta Chim. Acad. Sci. Hung., 107, 139–45 (1981). In general, they are prepared by reacting a 2-substituted maionic derivative of formula (VIII):

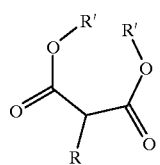

(VIII)

in which R has the above meanings and R' is a hydrogen or ($C_1$–$C_4$)alkyl group, with urea in the presence of a strong base such as for example an alkaline methoxide or ethoxide, in a solvent and at temperatures ranging from room temperature and the reflux temperature of the solvent. Preferred reaction conditions are the use of sodium methoxide in methanol at reflux.

The compounds of formula (VIII) on their turn are known or commercial products or can be prepared, for example, from the corresponding dialkyl malonate by condensation with a suitable R-X group, wherein X has the above meanings, in the presence of a base.

The intermediates of formula (III), (IV), (V), (VI), (VII) and (IX) are usually known compounds or can be prepared according to well known methodologies which are part of the general knowledge of the expert technician.

For example, compounds of formula (IV) can be obtained by functionalizing an 1.α-diamine on the nitrogen atoms or by reaching an α-chloro- or bromo-amine with an other amine optionally in the presence of an excess of the same amine of another base.

Compounds of formula (V) are aminoacids and can be natural or synthetic aminoacids These latter can be prepared for example according to the methods described in R. M. Williams. "Synthesis of Optically Active I-Aminoacids". Pergamon Press. 1989.

Compounds of formula (VI) are urea or sulfamide derivatives and if necessary can be prepared by known methods which involve for example, for the urea derivatives, the reaction of an amine of formula $R^3R^4$NH with an isocyanate of formula $R^2$—N=C=O or the sequential reactions of phosgene or carbonyldiimidazole with amines of formula $R^3R^4$NH and $R^2$—$NH_2$, respectively.

The acylsulfamide derivatives are obtained, for example, by reaction of a substituted sulfamide of formula $R^3R^4$N—$SO_2$—NH($R^2$) with the acyl chloride of barbituric derivative, as described in J. Het. Chem., 15, 221 (1978). J. Chem. Soc. Perk. Trans., 4, 643–5 (1986) and Collect. Czechosi. Chem. Com, 49(4), 840–51 (1984), which are herein incorporated by reference. Other synthesis of sulfamide derivatives are described in Ber. Dtsch. Chem. Ges., 100, 2719 (1967), J. Med. Chem., 8, 766 (1965), J. Org. Chem., 54(24), 5824 (1989) and J. Med. Chem., 33, 585–91 (1990), which are also incorporated by reference.

BIOLOGICAL ACTIVITY OF THE COMPOUNDS OF THE INVENTION

The compounds of the present invention have been tested in a pharmacological "in vitro" test of inhibition of MMP8 (human neutrophil collagenase). Said test provides for the determination via fluorescence of the inhibition of the degradation of a fluorescent substrate (DNP-Pro-Leu-Gly-Leu-Trp-Ala-D-Arg-$NH_7$, M1855 Bachem) by means of the catalytic domain of MMP8.

Reagents: 1) DNP-substrate=DNP-Pro-Leu-Gly-Leu-Trp-Ala-D-Arg-$NH_2$ (M1855 Bachem), M. W. 977,1 g/mol, concentration 25 μM in DMSO, 2) measurement buffer=50 mM TRIS/100 mM NaCl/10 mM $CaCl_2.2H_2O$, adjusted at pH 7 6 with hydrochloric acid. 3) Enzyme=catalytic domain of MMP8 (92 Kda), concentration 0.055 mg/ml in TRIS buffer. Substrate and enzyme are maintained at 0° C. with ice bath.

Inhibition assay:
Total volume=1 ml of solution kept under stirring in a cuvette

| Control: | 0.98 ml DMSO |
| --- | --- |
| | 0.01 ml of DNP-substrate |
| | 0.01 ml of enzyme |
| Assay: | 0.98 ml DMSO |
| | 0.01 ml DNP-substrate |
| | 0.01 ml of enzyme |
| | 0.01 ml of inhibitor (10 μg/ml) |

It is measured the fluoresence at 346 nm both of the control solution (without inhibitor) and of the solution containing the inhibitor. The inhibition of the catalytic activity of MMP8 results in the decrease of the DNP-substrate bond's lysis, with related decrease of the fluorescence of the solution.

The percentage of inhibition is expressed by the following formula:

% Inhibition=100−(rel. unit/time$_{with\ inhibitor}$/rel. unit/time$_{control}$× 100)

By repeating the experiment at different concentrations of inhibitor it is possible to determine the $IC_{50}$ value.

The same test has been performed also on the MMP-9 (gelentinase 92 kD) and the selectivity between the two enzymes has been evaluated. Values of MMP-9/MMP-8 rate well below 1 are expected to give rise to less side toxic effects, since MMP-8 seems more involved in the regulation of vital functions that MMP-9 does.

Table 1 shows the biological results for some representative compounds of the invention in comparison with the known matrix mealloproteinase inhibitor batimastat:

TABLE 1

Inhibition of MMP-8 and MMP-9 catalytic domain

| compound | Example | MMP-8 $IC_{50}$ (nM) | MMP-9 $IC_{50}$ (nM) |
|---|---|---|---|
| 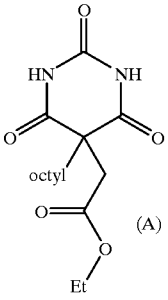 (A) | 1 | 107 | 19.6 |
| 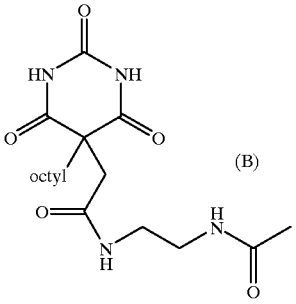 (B) | 5 | 99 | 20 |
| 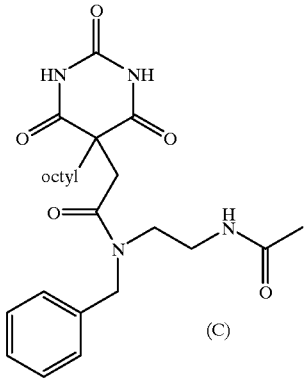 (C) | 6 | 68 | 14 |
| batimastat | — | 27 | 25 |

TABLE 1-continued

Inhibition of MMP-8 and MMP-9 catalytic domain

| compound | Example | MMP-8 $IC_{50}$ (nM) | MMP-9 $IC_{50}$ (nM) |
|---|---|---|---|
| 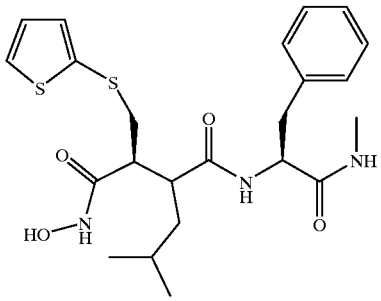 | | | |

The data clearly shown that the compounds of the invention exhibit an enhanced selectivity with respect to batimastat (MMP-9/MMP-8 rates from 0.18 to 0.2 vs. a value of 0.93 for batimastat). This means that they should not be endowed with the typical toxicity that limits the use of matrix metalloproteinase inhibitors in the man.

The compounds of the present invention have also shown activity in a test of chemoinvasion. In the test of chemoinvasion the Costar Transwell chambers for cell culture (diameter: 6.5 mm: pore size: 8 µm) are coated with 100 µl of Type IV collagen (diluted solution 50 µg/ml, then evaporation overnight). With the same procedure the chambers are coated with a second layer of Type IV collagen (100 µl of solution at concentration 50 µg/ml). Before use, the chambers are rinsed twice with sterile water and incubated for about 1 hour at 37° C. in a serum-free medium (DMEM).

The human fibrosarcoma HT1080 cells are harvested by trypsin-EDTA treatment, washed with DMEM-10% FCS and incubated for at least 30 minutes at 37° C. in the same medium. The cells are then washed with serum-free DMEM and resuspended in serum-free DMEM added with 0.1% BSA (fraction V), counted and diluted to obtain a final density of $3 \times 10^5$ cell/ml.

Preincubated inserts are aspirated to remove the serum-free medium. The lower compartment of the chambers is filled with 600 µl of DMEM-20% FCS-1% BSA (fraction V)-compound to test. 200 µl of cell suspension ($6 \times 10^4$ cells) containing the compound to test are added to the upper compartment and the chambers are incubated at 37° C. under humid atmosphere with $CO_2$. After first 24 hour incubation the media from both lower and upper compartments are replaced by fresh suspensions and the chambers are incubated for additional 24 hours.

Incubated filters are then washed with PBS, the cells are fixed 15 min. in 4% paraformaldehyde, permeabilized in methanol (10 minutes, −20° C.) and stained with May-Grunwald-Giemsa. Cells which adhere to the top of the filters are removed with a cotton swab, filters are detached from the bottom of the chambers and analyzed with microscope to determine the number of cells on the lower side of the filters.

In a control experiment in absence of metallo-proteinase inhibitor. HT1080 cells, which overexpress metalloproteinases, are able to degrade Type IV collagen and to migrate to the lower side of the filters. In the experiment with the inhibitor however the activity of the metalloproteinases is partially or totally inhibited and the number of cells which migrate to the lower side of the filters is decreased. The result of the experiment is expressed as percent of inhibition of chemoinvasion in the experiment with the metalloproteinase inhibitor (0% of inhibition in the control experiment).

Compound (C) (R=octyl; A=—N(Bn)—(CH$_2$)$_2$—NHCOMe) has shown 73% inhibition of chemoinvasion at a concentration $10^{-7}$ M, which can be compared with a 77% inhibition of the known metalloproteinase inhibitor GI 129471 (WO 90/05719 by British Bio-Technology Ltd.):

GI 129471

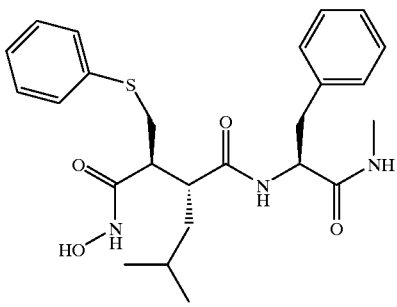

From what it is said above it appears that the compounds of the invention, in addition to their application in cancer therapy, may be used in the treatment of the conditions associated with the elevated or uncontrolled activity of the metzincins, as it is named the common family of zinc endopeptidases with high structural analogy which encompasses the MMPs, the astacins, the adamalysisns and the serralysisns. Examples of the diseases that can be treated with the compounds of the invention are inflammation, fibrosis, rheumatoid arthritis, osteoarthritis, atherosclerotic plaque rupture, aortic aneurism, heart failure, restenosis, septic arthritis, ulceration of the cornea, epidermic or gastric ulcerations, coronary thrombosis, proteinuria, pathological consequences of traumas, emphysema, multiple sclerosis, osteoporosis, periodontal disease or even as contraceptive agents.

The compounds of the present invention can be administered in doses ranging from 0.01 mg to 0.4 g per kilogram of body weight daily. A preferred dosage regimen to obtain best results is that which provides for the use from about 1 mg to about 50 mg per kilogram of body weight daily, employing unitary doses so that to administer in 24 hours from about 70 mg to about 3.5 g of the active compound to a patient having approximately 70 kg of body weight. Such a dosage regiment may be adjusted to achieve the best therapeutical effect. For example, doses may be administered taking into account the therapeutical situation of the patient. The active compound may be administered by oral, intravenous, intramuscular or subcutaneous route.

The pharmaceutical compositions of the present invention contain therapeutical effective amounts of at least one compound of the invention in admixture with pharmaceutically compatible excipients.

Oral compositions will generally include an inert diluent or an edible carrier. They can be included in gelatin capsules or compressed into tablets. Other oral administration forms are capsules, pills, elixirs, suspensions or syrups.

The tablets, pills, capsules, and similar compositions can contain the following ingredients (in addition to the active compound): a binder such as microcrystalline cellulose, tragacanth or gelatin; an excipient such as starch or lactose; a disintegrating agent such as alginic acid, primogel, maize starch and the like; a lubricant such as magnesium stearate; a fluidifier such as colloidal silicon dioxide; a sweetening agent such as sucrose or saccharine or a flavoring agent such as mint flavor, methyl salicylate or orange flavor. When the composition selected is in form of capsules, it can contain in addition a liquid carrier such as a fat oil. Other compositions can contain various material which change the physical form thereof, for example coating agents (for tablets and pills) such as sugar or shellac. The material used in the preparation of the compositions should be pharmaceutically pure and non toxic at the used dosage.

For the preparation of pharmaceutical compositions for the parenteral administration, the active ingredient can be included in solutions or suspensions, which can comprise in addition the following components: a sterile diluent such as water for injections, saline solution, oils, polyethylene glycols, glycerin, propylene glycol or other synthetic solvents: antibacterial agents such as benzyl alcohol; antioxidants such as ascorbic acid or sodium bisulfite; chelating agents such as ethylenediaminotetracetic acid; buffers such as acetates, citrates or phosphates and agents for adjusting the tonicity of the solution, such as sodium chloride or dextrose. The parental preparation can be included in amphoules, mono-dose syringes, glass or plastic vials.

The following examples further illustrate the invention.
Preparation 1-N-benzyl—N'-acetylethylenediamine To a solution of benzaldehyde (2 ml) in 40 ml of absolute ethanol, kept under nitrogen atmosphere and at room temperature is added N-acetylethylenediamine (2.2 ml) and stirring is continued for 18 hours. Successively is added portionwise sodium borohydride (969 mg) under vigorous stirring. After 1 hour the reaction mixture is cooled to 0° C. and quenched by dropwise addition of 6N hydrochloric acid (approx. 6 ml) until gas evolution has ceased. The solvent is evaporated and the resulting residue is dissolved in water (25 ml) and acidified with 6N hydrochloric acid until pH1.5–2 is reached. The acidic aqueous phase is extracted twice with ethyl acetate (2×25 ml) to remove some impurities, then is basified to pH 11 with 20% sodium hydroxide and further extracted twice with diethyl ether (2×50 ml). The pooled organic phases are dried over sodium sulfate and concentrated to dryness to give 1.367 g of the product as a clear oil which on standing solidifies.

TLC [SiO$_2$, eluant: chloroform/methanol/ammonium hydroxide 95:5:0.5)] detection u.v. and I$_2$ $^1$H-NMR in CDCl$_3$: 1.40 ppm (bs, 1 H); 1.98 ppm (s, 3 H); 2.78 ppm (t, 2 H); 3.35 ppm (q, 2 H); 3.80 (s, 2 H); 6.05 (bs, 1 H); 7.30–7.40 (m, 5 H);

$^{13}$C-NMR in CDCl$_3$; ppm 140 10; 128.46, 128.33, 128.04, 127.09, 126.84, 53.51, 48.79, 47.96, 39.16, 23.26.

Preparation 2-5-(4-methoxyphenyl)barbituric acid a) preparation of ethyl 4-methoxyphenylacetate A solution of 4-methoxyphenylacetic acid (2 g) and para-toluensulfonic acid (230 mg) in 30 ml of ethanol is refluxed for 2 hours. The solvent is evaporated under reduced pressure and the residue is suspended in a saturated aqueous solution of sodium hydrogencarbonate and extracted twice with ethyl acetate. The organic extracts are collected, washed with water and dried over sodium sulfate to give, after evaporation of the solvent under reduced pressure, 2.14 g of the product.

b) preparation of ethyl 4-methoxyphenyl malonate

A mixture of ethyl 4-methoxyphenylacetate (27.8 g) and sodium (3.68 g) in 90 ml of diethylcarbonate is refluxed for 3 hours, then the solvent is evaporated under reduced pressure and the residue is diluted with water and neutralized with acetic acid. The aqueous phase is extracted twice with diethyl ether. The organic extracts are pooled and washed twice with 1 N sodium hydroxide and once with water, then the organic phase is dried over sodium sulfate and concentrated to dryness. 34.2 g of the product are obtained.

c) preparation of 5-(4-methoxyphenyl)barbituric acid

To a solution of 660 mg of sodium in 50 ml of ethanol are added 3.86 g of ethyl 4-methoxyphenyl malonate and 1.28 g of urea. The reaction mixture is refluxed for 3 hours. A white solid separates, which is collected by filtration and redissolved in 15 ml of water. The solution is acidified to pH=1–2 by adding 6 N hydrochloric acid. A white solid separates, which is filtered and washed on the filter with water. After drying under vacuum at 50° C. for several hours, 2.28 g of the product are obtained.

Preparation 3-5-[3-(4-methoxyphenyl)propyl]barbituric acid a) preparation of 3-(4-methoxyphenyl)propionyl chloride To a suspension of 3-(4-methoxyphenyl)propionic acid (10 g) in 150 ml of toluene are added 8 ml of thionyl chloride and the mixture is heated to 65° C. for 4 hours. The solvent is evaporated off under reduced pressure and the residue is redissolved in toluene and concentrated to dryness. Such a step is repeated twice. 11 g of the product are obtained as a yellow oil.

b) preparation of 5-[3-(4-methoxyphenyl)propionyl] barbituric acid

To a suspension of barbituric acid (6.4 g) in 48 ml of pyridine are added dropwise 11 g of 3-(4-methoxyphenyl) propionyl chloride and the mixture is stirred at room temperature for 18 hours. The reaction mixture is then poured into ice and acidified to pH=1 by adding 6 N hydrochloric acid. A solid precipitates, which is filtered and resuspended in methanol. The suspension is kept under stirring for 15 minutes, then the solid is recovered by filtration to give 12.2 g of the product, m.p. 248–250° C.

c) preparation of 5-[3-(4-methoxyphenyl)propyl] barbituric acid

To a suspension of 10 g of 5-[3-(4-methoxyphenyl) propionyl]barbituric acid in 100 ml of acetic acid are added portionwise 4.5 g of sodium cyanoborohydride, then the mixture is heated to 60° C. After 1 hour the reaction mixture is cooled to room temperature and poured into ice. After 30 minutes a solid is recovered by filtration, which is dried under vacuum at 50° C. to give 8.74 g of the product, m.p. 195–197° C.

Preparation 4-5-benzylbarbituric acid a) preparation of 5-benzylidenebarbituric acid A suspension of 5 g of barbituric acid in 50 ml of water is heated until a compklete dissolution occurs, then it is added with 4.3 ml of benzaldehelde. The mixture is refluxed for 1 hour, then the solid which separated is filtered, washed several times with water and dried under vacuum at 100° C. to give 8.17 g of the product. m.p.>258° C.

b) preparation of 5-benzylbarbituric acid

To a suspension of 5-benzylidenebarbituric acid (4 g) in 200 ml of methanol are added portionwise 1.4 g of sodium borohydride. After 10 minutes from the end of the addition, 100 ml of water are added and the mixture is acidified with 1 N hydrochloric acid to pH=2. The solvent is evaporated off and the aqueous phase is extracted with ethyl acetate. The pooled extracts are dried over sodium sulfate and concentrated to dryness. 3.6 g of the product crystallize. m.p. 207–209° C.

Preparation 5-5-(4-hydroxyphenyl)barbituric acid

To a suspension of 5-(4-methoxyphenyl)barbituric acid (222 mg) in 5 ml of methylene chloride, kept at −5/−10° C. and under nitrogen atmosphere, is dropped a solution of boron tribromide (473 μl) in 2 ml of methylene chloride. The stirring is continued for additional 2 hours at −5° C., then the temperature is brought to room temperature and stirring is continued for further 20 hours. The reaction mixture is again cooled to 0° C. with an ice bath and it is basified to pH=9–10 by adding dropwise 5% sodium hydroxide. The aqueous phase is separated, filtered through a celite plug, cooled with ice bath and acidified to pH=1 with 37% hydrochloric acid. A white solid separates which after 1 hour is separated by filtration and dried under vacuum at 60° C. to give 215 mg of the product.

Preparation 6-5-(4-methylphenyl)barbituric acid

To a solution of sodium (184 mg) in 12 ml of ethanol are added 0.95 ml of diethyl 2-(4-methylphenyl)malonate and 360 mg of urea, then the mixture is refluxed for 3 hours. A white solid separates, which is filtered and redissolved in 4 ml of water. The solution is acidified to pH=1–2 by adding 6 N hydrochloric acid. A white solid separates, which is collected by filtration, washed with 15 ml of water and dried under vacuum. 619 mg of the product are obtained. m.p. 271° C.

Preparation 7-5-octylbarbituric acid a) preparation of diethyl 2-octylmalonate

To a solution of 2.63 of sodium in 100 ml of ethanol is added dropwise a solution of 19.1 ml of diethylmalonate in 10 ml of ethanol. The mixture is successfully added with 20.4 ml of 1-bromooctane dissolved in 10 ml of ethanol, then the mixture is refluxed for 6 hours. The reaction mixture is concentrated to a little volume and the residue is partitioned between a saturated aqueous solution of sodium hydrogenphosphate (200 ml) and ethyl acetate (200 ml). The organic phase is washed with 75 ml of water and 75 ml of saturated aqueous solution of sodium chloride, dried over sodium sulfate and concentrated to dryness to give 31.8 g of the product as an oil.

$^1$H-NMR in CDCl$_3$: 0.80–0.95 ppm (m, 3 H); 1.15–1.40 ppm (m, 18 H); 1.88 ppm (q, 2 H); 3.33 ppm (t, 1 H); 4.19 ppm (q, 4 H).

b) preparation of 5-ocrylbarbituric acid

To a solution of sodium (5.32 g) in 400 ml of anhydrous ethanol is added a solution of diethyl 2-ocrylmalonate (31.5 g) in 50 ml of ethanol and successively 10.27 g of urea, then the mixture is refluxed for 2 hours 30 minutes. The mixture is rapidly cooled to room temperature and the solid which was formed is recovered by filtration and washed with diethyl ether. The solid is then dissolved in 200 ml of water and acidified with 6 N hydrochloric acid until pH 1.5–2 is reached. A solid separates. The mixture is added with 200 ml of ethyl acetate and is stirred for 2 hours, then it is added with additional 800 ml of warm ethyl acetate. The organic phase is separated and the aqueous phase is washed with 200 ml of ethyl acetate. The pooled organic phases are washed with 250 ml of saturated aqueous solution of sodium chloride, dried over sodium sulfate and concentrated to dryness. 21.03 g of the product are obtained.

$^1$H-NMR in d6-DMSO; 0.77–0.80 ppm (m, 3 H); 1.23 ppm (s, 12 H); 1.80–1.95 ppm (m, 2 H); 3.52 ppm (t, 1 H); 11.15 ppm (s, 2 H).

Preparation 8-5-naphtylbarbituric acid a) preparation of ethyl 2-naphtylacetate

To a solution of 2-naphtylacetic acid (5 g) in 50 ml of ethanol are added 0.5 g of paratoluensulfonic acid, then the reaction mixture is refluxed for about 4 hours. The solvent is evaporated off and the residue is dissolved in diethyl ether, washed twice with a saturated aqueous solution of sodium hydrogencarbonate and once with brine, then the pooled organic extracts are dried over sodium sulfate and concentrated to dryness. 5.64 g of the product as a yellow oil are obtained.

b) preparation of diethyl 2-naphtylmalonate

To a solution of ethyl 2-maphtylacetate (2 g) in 23.3 ml of diethylcarbonate, kept under stirring and at room temperature, are added portionwise 0.232 g of sodium. The reaction mixture is refluxed for 2 hours 30 minutes, then it is concentrated in order to eliminate the not reacted diethylcarbonate and it is added with 20 ml of cold water. The resulting mixture is acidified with acetic acid until weak acidity is reached, then it is extracted three times with diethyl ether. The pooled organic extracts are dried over sodium sulfate and the solvent is evaporated off, to give, after recrystallization from diethyl ether (19 ml). 1.015 g of the product as a white solid.

c) preparation of 5-naphtylbarbituric acid

A solution of sodium (0.32 g) in 30 ml of anhydrous ethanol is added with diethyl 2-naphtylmalonate (2 g) and successively with urea (0.63 g). The mixture is refluxed for 2 hours, then the solid which is separated is recovered by filtration, the it is dissolved in 7 ml of water and acidified to pH=1 with 6 N hydrochloric acid. A white solid precipitates which, after 30 minutes under stirring, is filtered and washed with water. The solid is dried overnight under vacuum at 40° C., to give 0.96 g of the product.

Preparation 9-5-(4'-biphenyl)barbituric acid a) preparation of ethyl (4'-biphenyl)acetate A suspension of (4'-biphenyl)acetic acid (6.4 g) in 60 ml of ethanol is added with 1.1 g of para-toluensulfonic acid, then the reaction mixture is refluxed for 4 hours 30 minutes. The solvent is evaporated off, the residue is dissolved in diethyl ether and the resulting organic phase is washed three times with a saturated aqueous solution of sodium hydrogencarbonate and once with brine. The organic phase is then dried over sodium sulfate and the solvent is evaporated off to give 7.1 g of the product as a yellow oil.

b) preparation of diethyl (4'-biphenyl)malonate

A solution of ethyl (4'-biphenyl)acetate (7.1 g) in 60 ml of diethylcarbonate, kept under nitrogen atmosphere, is added portionwise with sodium (0.734 g), then it is heated at 120° C. for 3 hours. The solvent is evaporated off and the residue is dissolved in 65 ml of cold water and acidified with acetic acid until pH=5–6 is reached. The aqueous phase is then extracted three times with diethyl ether and the pooled organic extracts are dried over sodium sulfate and concentrated to dryness. The residue is purified by silica gel chromatography (eluent: petroleum ether/diethyl ether 9.4:0.6) to give 7.05 g of the product. m.p. 51–53° C.

c) preparation of 5-(4'-biphenyl)barbituric acid

A solution of sodium (0.322 g) in 40 ml of anhydrous ethanol is added with diethyl (4'-biphenyl)malonate (2.2 g) and successively with urea (0.63 g). The reaction mixture is refluxed for 3 hours 30 minutes, then it is cooled to room temperature and the solid is recovered by filtration. The obtained solid is redissolved in 40 ml of warm water and the resulting aqueous phase is acidified to pH=1 with 6 N hydrochloric acid. The solid which separates is kept 15 minutes under stirring, then it is filtered and dried under vacuum at 60° C. 1.1 g of the product are obtained. m.p.>240° C.

Preparation 10-5-(4'phenoxyphenyl)barbituric acid a) preparation of N-[(4'-phenoxybenzyl)thiocarbonyl] morpholine A mixture of (4'-phenoxyphenyl)methylketone (19.1 g), morpholine (20 ml) and sulphur (4.32 g) is refluxed for 24 hours, the it is extracted with diethyl ether. The organic phase is concentrated to dryness to give, after crystallization form a petroleum ether/ethyl acetate mixture 8:2 (600 ml), 12.2 g of the product. m.p. 75–77° C.

b) preparation of (4'-phenoxyphenyl)acetic acid

A suspension of N-[(4'-phenoxybenzyl)thiocarbonyl] morpholine (1.725 g) in 87 ml of 10% potassium hydroxide is refluxed for 8 hours 30 minutes, then the reaction mixture is brought to room temperature and acidified with 1N hydrochloric acid. A white solid separates, which is stirred for 30 minutes and filtered. The solid washed with water and dried under vacuum, to give 1.095 g of the product. m.p. 70–72° C.

c) preparation of ethyl (4'-phenoxyphenyl)acetate

To a suspension of (4'-phenoxyphenyl)acetate acid (0.456 g) in 4 ml of ethanol is added para-toluensulfonic acid (0.076 g) and the resulting mixture is refluxed for 2 hours. The solvent is evaporated off, the residue is dissolved in diethyl ether and the organic phase is washed with saturated aqueous solution of sodium hydrogencarbonate and then with brine. The organic phase is dried over sodium sulfate and concentrated to dryness to give 0.458 g of the product as a brown oil.

d) preparation of 5-(4'-phenoxyphenyl)barbituric acid

A solution of sodium ethoxide (0.27 g) in 3 ml of anhydrous ethanol is added with 0.657 g of ethyl (4'-phenoxyphenyl)acetate dissolved in 5 ml of ethanol, then with urea (0.18 g). The reaction mixture is refluxed for 2 hours 30 minutes, then it is cooled to room temperature and the suspended solid is filtered. The solid is redissolved in 8 ml of water and the solution is acidified with 1 N hydrochloric acid. The solid which separates is recovered by filtration to give 0.165 g of the product. m.p.>240° C.

Preparation 11-5-decylbarbituric acid a) preparation of diethyl decylmalonate

A solution of sodium (0.46 g) in 10 of anhydrous ethanol is added with 3.35 ml of diethyl malonate in 3 ml of ethanol and successively with a solution of dicylbromide (4.15 ml) in 3 ml of ethanol. The reaction mixture is refluxed for 4 hours, then the precipitate is filtered off and the filtrate is concentrated to dryness. The residue is redissolved in a saturated aqueous solution of sodium hydrogensulfate and it is extracted with ethyl acetate. The organic extract is dried over sodium sulfate and the solvent is evaporated off. The resulting residue is used as such in the successive reaction.

b) preparation of 5-decylbarbituric acid

To a solution of diethyl decylmalonate of step a) in 40 ml of ethanol are added 2.72 g of sodium ethoxide and then 1.8 g of urea. The reaction mixture is refluxed for 2 hours, then the precipitate is filtered and redissolved in 40 ml of water. The resulting aqueous solution is acidified with 6 N hydrochloric acid. The solid which separates is recovered by filtration and dried under vacuum at 40° C. overnight, to give 2.152 g of the product. m.p. 190° C.

Example 1

5-octyl-5-(ethoxycarbonylmethyl)barbituric acid 4.05 g of 5-octylbarbituric acid (preparation 7) are dissolved in 25 ml of dimethylformamide, 1.16 g of sodium carbonate are added. Ethyl bromoacetate (2.25 ml) is added dropwise to the reaction mixture in 5 minutes, then the mixture is kept at room temperature under stirring for about 3 hours. The reaction mixture is then partitioned between 400 ml of water, 17 ml of 1 N hydrochloric acid and 150 ml of ethyl acetate. The organic phase is separated and washed with 150 ml of water and 100 ml of brine, then it is dried over sodium sulfate. The aqueous phases are extracted with 100 ml of ethyl acetate and the organic extracts are pooled, dried over sodium sulfate and evaporated to dryness, to give 6.5 g an oily residue. This residue is purified by silica gel chromatography (eluant methylene chloride/ethyl acetate 9 1) to give 3.87 g of the product.

Elem. Anal. (% found/calcd): C 58.79/58.88; H 8.04/8.03, N 8.47/8.58

$^1$H-NMR in CDCl$_3$, 0.80–-0.95 ppm (m, 3 H); 1.15–1.40 ppm (m, 15 H); 1.80–1.95 ppm (m, 2 H); 3.18 ppm (s, 2 H); 4.12 ppm (q, 2 H); 8.68 ppm (s, 1 H)

Example 2

5-octyl-5-(carboxymethyl)barbituric acid 3.29 g of the ester of example 1 are dissolved in 35 ml of 1 N sodium hydroxide and the solution is kept under stirring at room temperature for abou 16 hours, then it is quenched by addition of 6 ml of 6 N hydrochloric acid. A white solid separates, which is kept under stirring for about 5 hours, then it is collected by filtration, washed with 0.05 M hydrochloric acid and water and finally dried under vacuum at 40 ° C. 2.84 g of the product are obtained as a white solid.

Elem. Anal. (% found/calcd): C 55.63/56.36, H 7.39/7.43, N 9.18/9.39

$^1$H-NMR in DMSO-d$_n$: 0.80–0.95 ppm (m, 3 H); 1.00–1.35 ppm (s, 12 H); 1.60–1.80 ppm (m, 2 H); 2.90 ppm (s, 2 H); 11.42 ppm (s, 2 H); 12.75 ppm (br s, 1 H).

Example 3

5-octyl-5-(carboxymethyl)barbituric acid hydroxysuccinimide ester

To a solution of 5-octyl-5-(carboxymethyl)barbituric acid (103 mg, example 2) and N-hydroxysuccinimide (60 mg) in 2.5 ml of anhydrous tetrahydrofuran, kept under nitrogen atmosphere and cooled at 0–5° C. is added morpholinoethyl isonitrile (71 μl) via syringe. The mixture is allowed to warm to room temperature and is stirred for 70 hours. The reaction mixture is concentrated to a little volume and the residue is partitioned between 0.1 N hydrochloric acid (20 ml) and ethyl acetate (25 ml). The organic phase is washed with 20 ml of saturated aqueous solution of sodium chloride and dried over sodium sulfate. Removal of the solvent affords 130 mg of crude product, which is purified by column chromatography (SiO$_2$, eluant: dichloromethane/ethyl acetate 75 25) to give 60 mg of pure product as white amorphous solid.

$^1$H-NMR in CDCl$_3$: 0.80–0.95 ppm (m, 3 H); 1.15–1.40 ppm (s, 12 H); 1.80–1.95 ppm (m, 2 H); 2.75 ppm (s, 2 H); 3.40 ppm (s, 2 H); 9.28 ppm (s, 2 H)

$^{13}$C-NMR in CDCl$_3$, ppm 171.06; 169.06; 166.84; 149.15; 52.87; 39.49; 36.50; 31.65; 29.21; 29.05; 29.00; 25.49; 23.96; 22.51; 14.11

Example 4

5-octyl-5-(carboxymethyl)barbituric acid N-benzyl amide

Method A

To a solution of 5-octyl-5-(carboxymethyl)barbituric acid hydroxysuccinimide ester (58 mg, example 3) in 1.5 ml of acetonitrile, kept under nitrogen atmosphere and at room temperature, is added benzylamine (40 μl), then the mixture is stirred at room temperature for 3.5 hours. The reaction mixture is concentrated to a little volume and the residue is partitioned between 0.1 N hydrochloric acid (10 ml) and ethyl acetate (10 ml). The organic phase is washed with 10 ml of saturated aqueous solution of sodium bicarbonate, successively with 10 ml of saturated aqueous solution of sodium chloride and dried over sodium sulfate.

Removal of the solvent affords 47 mg of crude product as white solid.

Method B

To a solution of 5-octyl-5-(carboxymethyl)barbituric acid (208 mg; example 1) in 2.5 ml of anhydrous tetrahydrofuran, kept under nitrogen atmosphere and cooled at 0–5° C. is added 1.1'-carbonyldiimidazole (124 mg). The mixture is allowed to warm to room temperature and is stirred for 4 hours. Then benzylamine (76 μl) is added and stirring is continued for 20 hours. The reaction mixture is concentrated to dryness and the residue is partitioned between 0.1 N hydrochloric acid (10 ml) and ethyl acetate (15 ml). The organic phase is washed with 10 ml of saturated aqueous solution of sodium chloride and dried over sodium sulfate.

Removal of the solvent affords 265 mg of crude product, which is purified by column chromatography (SiO$_2$, eluant: dichloromethane/ethyl acetate 8:2) to give 220 mg of pure product as white solid.

$^1$H-NMR in DMSO-d$_6$: 0.77–0.90 ppm (m, 3 H); 1.23 ppm (s, 12 H); 1.60–1.75 ppm (m, 2 H); 2.95 ppm (s, 2 H); 4.15–4.25 ppm (d, 2 H); 7.15–7.40 ppm (m. 5 H); 8.55 ppm (t, 1 H); 11.32 ppm (s, 2 H)

$^{13}$C-NMR in DMSO-d$_6$, ppm 173.36, 169.39, 150.36, 139.01, 128.24, 127.05, 126.77, 51.57, 42.05, 41.52, 38.10, 31.12, 28.67, 28.51, 28.42, 23.54, 22.00, 13.89

Elem. Anal(% found/calcd) C 65.13/65.09; H 7.46/7.54; N 10.84/10.85.

Example 5

5-octyl-5-(carboxymethyl)barbituric acid N'-acetyl N-ethylenediamide

To a solution of 5-octyl-5-(carboxymethyl)barbituric acid (246 mg; example 2) in 3 ml of anhydrous tetrahydrofuran, kept under nitrogen atmosphere and cooled at 0–5° C. is added 1,1'-carbonyldiimidazole (147 mg). The mixture is allowed to warm to room temperature and is stirred for 4 hours. Then N-acetylethylenediamine (88 μl) is added, after 30 minutes a white solid separates, then stirring is continued for 20 hours. The reaction mixture is concentrated to dryness and the residue is partitioned between 0.1 N hydrochloric acid (10 ml) and ethyl acetate (20 ml). The mixture is warmed until a complete solution is obtained then the organic phase is separated, washed with 10 ml of saturated aqueous solution of sodium chloride and dried over sodium sulfate.

Removal of the solvent affords 295 mg of crude product, which is purified by crystallization from ethyl acetate/ethanol (10 ml/2.5 ml) to give 199 mg of pure product as white solid.

$^1$H-NMR in DMSO-d$_6$, 0.77–0.90 ppm (m, 3 H); 1.23 ppm (s, 12 H); 1.60–1.75 ppm (m, 2 H); 1.78 ppm (s, 3 H); 2.83 ppm (s, 2 H); 2.90–3.00 ppm (m, 4 H); 7.75–7.85 ppm (m, 1 H), 8.00–8.10 ppm (m, 1 H); 11.25 (s, 2 H)

$^{13}$C-NMR in DMSO-d$_6$: ppm 173.32; 169.48; 169.30; 150.36; 41.47; 41.59; 38.34; 38.07; 31.11; 28.66; 28.50; 28.41; 23.53; 22.57; 22.00

Elem. Anal. (% found/calcd) C 55.75/56.53; H 7.90/7.91; N 14.36/14.65

Example 6

5-octyl-5-(carboxymethyl)barbituric acid N'-acetyl-N-benzyl-N-ethylenediamide 5-octyl-5-(carboxymethyl)barbituric acid (215 mg; example 2) is suspended in thionyl chloride (3 ml) and the mixture is refluxed for 1 hour. The resulting solution is concentrated to a small volume, diluted with anhydrous toluene and evaporated to dryness. The obtained residue is taken up in dichloromethane (2 ml) and to the resulting solution, kept under nitrogen atmosphere and cooled to 0° C. is added N-benzyl-N'-acetylethylenediamine (180 mg; preparation 1) in one portion and successively pyridine (0.5 ml). The reaction mixture is stirred for 1.5 hours, then it is concentrated to a little volume and the residue is partitioned between 1N hydrochloric acid (3 ml) and diethyl ether (3 ml). A white solid separates from the mixture which is recovered by filtration and successively washed on the filter with water and ethyl acetate. The isolated precipitate is dissolved on warming in ethyl acetate (20 ml) and the resulting solution is dried over sodium sulfate and concentrated to dryness. The obtained residue is triturated with ethyl acetate at reflux to give 180 mg of the product as white solid.

TLC [$SiO_2$, eluant: chloroform/methanol 85:15]: detection u.v. and $I_2$ m.p.=184.5–185.5° C.

$^1$H-NMR in DMSO-$d_6$, 0.80–0.95 ppm (m, 3 H); 1.10–1.35 ppm (s, 12 H); 1.60–1.80 ppm (m, 2 H); 1.70 and 1.85 ppm (two s: 3 H); 3.00–3.30 ppm (m, 4 H); 3.35 ppm (s, 2 H); 4.45 and 4.60 ppm (two s, 2 H); 7.05–7.45 ppm (m 5 H); 7.80 and 8.00 ppm (two t, 1 H); 11.28 ppm (s, 2 H)

Elem. Anal. % found/calcd): C 64.10/63.54: H 7.89/7.68; N 11.62/11.86.

Example 7

According to the procedures described in the previous preparations and examples, starting from the suitable starting materials, the following barbituric acid derivatives are obtained -5-octyl-5-(carboxymethyl)barbituric acid N'-acetyl-N-benzyl-N-ethylenediamide;

-5-(4'-diphenyl)-5-(carboxymethyl)barbituric acid N-benzopiperidinone;

-5-(4'-phenoxyphenyl)-5-(carboxymethyl)barbituric acid N'-acetyl-N-benzyl-N-ethylenediamide;

-5-decyl-5-(carboxymethyl)barbituric acid N'-acetyl--N-ethyleneamide;

-5-octyl-5-(carboxymethyl)barbituric acid benzyl ester;

-5-octadecyl-5-(carboxymethyl)barbituric acid N'-acetyl-N-benzyl-N-ethylenediamide;

-5-octyl-5-(carboxymethyl)barbituric acid N'-methansulphonyl-N-benzyl-N-ethylenediamide;

-5-octyl-5-(carboxymethyl)barbituric acid 2-(N'-phtalamido)-N-ethylamide;

-5-octyl-5-(carboxymethyl)barbituric acid 2-(N'-piperidine-2,3-dione)-N-ethylamide;

-5-octyl-5-(carboxymethyl)barbituric acid 2-(N'-caprolactam)-N-ethylamide;

-5-octyl-5-(carboxymethyl)barbituric acid 2-(N'-pyrrolidinone)-N-ethylamide;

-5-octyl-5-(carboxymethyl)barbituric acid N-amidoglycine ethyl ester;

-5-octyl-5-(carboxymethyl)barbituric acid N-amidophenylalanine ethyl ester;

-5-octyl-5-(carboxymethyl)barbituric acid N-amidotriptophane methyl ester;

-5-octyl-5-(carboxymethyl)barbituric acid N-amidophenylalaninamide;

-5-octyl-5-(carboxymethyl)barbituric acid N-amidophenylalanin-(N'-benzyl)-amide;

-5-octyl-5-(carboxymethyl)barbituric acid N-amidoglycyl ((L)-phenylalaninamide);

-5-octyl-5-(aminocarbonylaminocarbonylmethyl) barbituric acid;

-5-octyl-5-(aminosulphonylaminocarbonylmethyl) barbituric acid;

-5-5-[(N-pyrrolidinyl)carbonylaminocarbonylmethyl] barbituric acid;

-5-octyl-5-[(N-piperazinyl) carbonylaminocarbonylmethyl]barbituric acid;

-5-octyl-5-[(N-thiomorpholinyl) carbonylaminocarbonylmethyl]barbituric acid.

What is claimed is:

1. A compound of formula I

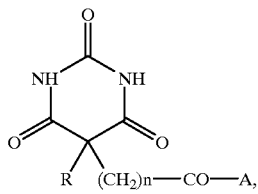

wherein

R is selected from the group consisting of ($C_6$–$C_{20}$) alkyl, biphenyl, phenoxyphenyl and ($C_1$–$C_4$) alkoxyphenyl, n is 1 and A is selected from the group consisting of
(a) hydroxyl,
(b) ($C_1$–$C_4$) alkoxy,
(c) benzylamino,
(d) an oxy-succinamido group,
(e) —N($R_2$)—($CH_2$)$_m$—N($R_9$)—T—$R_{10}$ in which m is 2–6; $R_2$ is hydrogen or a ($C_1$–$C_4$) alkyl, phenyl or benzyl group; $R_9$ is hydroxy, and $R_{10}$ is ($C_1$–$C_{10}$) alkyl or $R_9$ and $R_{10}$ form together with a N—CO group to which they are linked a phtalamido, piperidinedione, caprolactame or pyrrolidinone ring, and T is CO or $SO_2$ or
(f) —NH—T—N$R_3R_4$ in which T is CO or $SO_2$ and $R_3$ and $R_4$ are each hydrogen, or $R_3$ and $R_4$ together with nitrogen form a pyrroline, a piperazine or a thiomorpholine ring; and enantiomers, racemates, diastereoisomers, tautomers or a mixture thereof, of a salt thereof, with a pharmaceutically acceptable acid or base.

2. The compound according to claim 1, wherein A is —N($R_2$)—($CH_2$)$_m$—N($R_9$)—T—$R_{10}$ in which $R_2$ is hydrogen or a benzyl group, m is 2, $R_9$ is hydrogen, T is CO and $R_{10}$ is ($C_1$–$C_{10}$)alkyl.

3. The compound according to claim 1, wherein R is an octyl, an decyl, an octadecyl, a biphenyl or a phenoxyphenyl group.

4. The compound according to claim 1, wherein the compound is selected from the group consisting of 5-octyl-5-(ethoxycarbonylmethyl)barbituric acid, 5-octyl-5-(carboxymethyl)barbituric acid, 5-octyl-5-(carboxymethyl)barbituric acid N-benzyl amide, 5-octyl-5-(carboxymethyl)barbituric acid N'-acetyl N-ethylenediamide, 5-octyl-5-(carboxymethyl)barbituric acid N'-acetyl N-ethylenediamide, 5-octyl-5-(carboxymethyl)barbituric acid N-benzopiperidinone, 5-(4'-diphenyl)-5-(carboxymethyl)barbituric acid N'-acetyl-N-benzyl-N-ethylenediamide, 5-(4'-phenoxyphenyl)-5-(carboxymethyl)barbituric acid N'-acetyl-N-benzyl-N-ethylenediamide, 5-decyl-5-(carboxymethyl)barbituric acid N'-acetyl-N-ethylenediamide, 5-octyl-5-(carboxymethyl)barbituric acid benzyl ester, 5-octadecyl-5-(carboxymethyl)barbituric acid N'-acetyl-N-benzyl-N-ethylenediamide, 5-octyl-5-(carboxymethyl)barbituric acid N'-methylsulphonyl-N-benzyl-N-ethylenediamide, 5-octyl-5-(carboxymethyl)barbituric acid 2-(N'-phtalamido)-N-ethylamide, 5-octyl-5-(carboxymethyl)barbituric acid 2-(N'-piperidine-2,3-dione)-N-ethylamide.

5-octyl-5-(carboxymethyl)barbituric acid 2-(N'-caprolactam)-N-ethlamide, 5-octyl-5-(carboxymethyl)barbituric acid 2-(N'-pyrroiidinone)-N-ethylamide, 5-octyl-5-(aminocarbonylaminocarbonylmethyl) barbituric acid, 5-octyl-5-(aminosulphonylaminocarbonylmethyl) barbituric acid, 5-octyl-5-[(N-pyrrolidinyl) carbonylaminocarbonylmethyl]barbituric acid, 5-octyl-5-[(N-piperazinyl) carbonylaminocarbonylmethyl]barbituric acid, 5-octyl-5-[N-thiomorpholinyl) carbonylaminocarbonylmethyl]barbituric acid, and 5-octyl-5-(carboxymethyl) barbituric acid hydroxysuccinimide ester.

5. A method for inhibiting metzincins, comprising administering a metzincin-inhibiting effective amount of a compound according to claim 1 to a patient in need thereof.

6. A method for inhibiting matrixmetalloproteases comprising administering a metalloproteinase-inhibiting effective amount of a compound according to claim 1 to a patient in need of such inhibition.

7. A method for inhibiting tumor growth and metastasis comprising administering a tumor and metastases inhibitory effective amount of a compound according to claim 1 to a patient in need of such inhibition.

8. A pharmaceutical composition comprising a compound according to claim 1, and a pharmaceutically acceptable carrier.

* * * * *